US005928903A

United States Patent [19]
Weir et al.

[11] Patent Number: 5,928,903

[45] Date of Patent: Jul. 27, 1999

[54] METHOD FOR EXPRESSING RECOMBINANT GENES IN BACTERIA IN ABSENCE OF ANTIBIOTIC SELECTION

[75] Inventors: Andrew Neil Charles Weir, Maidenhead; Andrew Mountain, Wokingham, both of United Kingdom

[73] Assignee: Celltech Therapeutics Limited, Berkshire, United Kingdom

[21] Appl. No.: 08/411,778

[22] PCT Filed: Jul. 22, 1993

[86] PCT No.: PCT/GB93/01547

§ 371 Date: Mar. 14, 1995

§ 102(e) Date: Mar. 14, 1995

[87] PCT Pub. No.: WO94/02607

PCT Pub. Date: Feb. 3, 1994

[30] Foreign Application Priority Data

Jul. 22, 1992 [GB] United Kingdom .................. 9215541

[51] Int. Cl.[6] .......................... A61K 39/395; C12N 15/00

[52] U.S. Cl. ..................... 435/69.6; 435/471; 435/252.3; 435/252.33; 435/71.2; 435/69.7; 530/387.3; 530/387.1; 536/23.53; 536/23.1; 514/12

[58] Field of Search ................................ 435/69.6, 69.7, 435/71.2, 252.3, 252.33, 471; 530/387.3, 387.1; 536/23.53, 23.1; 514/12

[56] References Cited

U.S. PATENT DOCUMENTS 5,015,573 5/1991 Yarrington et al. .................... 435/69.6

FOREIGN PATENT DOCUMENTS 0 121 386 10/1984 European Pat. Off. .
2 137 631 11/1986 United Kingdom .
WO 92/01059 1/1992 WIPO .
WO 94/13805 6/1994 WIPO .

OTHER PUBLICATIONS

Carter et al., "High Level *Escherichia coli* Expression and Production of a Bivalent Humanized Antibody Fragment", Bio/Technology, vol. 10, Feb. 1992, pp. 163–167.

Roberts et al., "Generation of an Antibody with Enhanced Affinity and Specificity for its Antigen by Protein Engineering", Nature, vol. 328, Aug. 1987, pp. 731–734.

Hashimoto–Gotoh et al., "Specific–purpose Plasmid Cloning Vectors", Gene, vol. 16, 1981, pp. 227–235.

Wright et al., "Dual–origin Plasmids Containing an Amplifiable ColE1 ori; Temperature–controlled Expression of Cloned Genes", Gene, vol. 49, 1986, pp. 311–321.

Helinski et al., "Partitioning of the pSC101 Plasmid During Cell Division", Plasmids in Bacteria, 1985, pp. 383–395.

*Primary Examiner*—Toni R. Scheiner
*Assistant Examiner*—Julie E Reeves
*Attorney, Agent, or Firm*—Foley & Lardner

[57] ABSTRACT

The invention provides a method for the expression of recombinant molecules in bacterial hosts in a defined medium in the absence of antibiotic selection. The method uses an expression vector comprising a regulatable promoter by which the production of foreign proteins may be controlled during the growth phase of the culture, an origin of replication maintaining medium vector copy number and a transcriptional terminator.

11 Claims, 11 Drawing Sheets

PLASMID MAPS FOR E.Coli EXPRESSION OF A5B7 FAB

BATCH GROWTH PROFILE OF STRAIN W3110 pMRR028
IN DEFINED MEDIUM SM6 PLUS GLUCOSE
INDUCTION BY LACTOSE FEEDING AT OD= 30

METHOD FOR EXPRESSING RECOMBINANT GENES IN BACTERIA IN ABSENCE OF ANTIBIOTIC SELECTION

This application is the national stage filing under 35 U.S.C. 371 of PCT/GB93/01547, filed Jul. 22, 1993.

FIELD OF THE INVENTION

This invention relates to a method for the expression of recombinant antibody genes in bacterial host cells in a defined medium in the absence of antibiotic selection.

DESCRIPTION OF BACKGROUND ART

The rapid developments in recombinant DNA techniques have resulted in the identification and isolation of many novel genes, some of known function and some of unknown function. Invariably there is a need to express the gene in a heterologous cell system in order to produce material for structure-function studies, diagnostic reagents such as monoclonal or polyclonal antibodies and material for in vivo activity testing and therapy.

Several alternative systems for the expression of foreign genes have been developed including systems based upon mammalian cells, insect cells, fungal cells, bacterial cells and transgenic animals or plants. The choice of expression system for a given gene depends upon the likely features of the encoded protein, for example any post-translational protein modifications needed for biological activity, as well as the objective of the study. Other important considerations for the investigator are the facilities available, time and cost involved in generating the amounts or recombinant protein required.

The most widely used and convenient system for the production of foreign proteins remains that based on the prokaryote *Escherichia coli.* The advantages of this system comprise the ease of gene manipulation, the availability of reagents including gene expression vectors, the ease of producing quantities of protein (up to a gramme in simple shake-flask culture), speed and the high adaptability of the system to express a wide variety of proteins.

Expression of any foreign gene in *E. coli* begins with the insertion of a cDNA copy of the gene into an expression vector. Many forms of expression vector are available. Such vectors usually comprise a plasmid origin of DNA replication, an antibiotic selectable marker and a promoter and transcriptional terminator separated by a multi-cloning site (expression cassette) and a DNA sequence encoding a ribosome binding site. The method of transcriptional regulation varies between the various promoters now available (ptac, λpL, T7). The ptac and T7 expression based systems are controlled by the chemical inducer IPTG, whilst the λ promoters are controlled by a temperature switch.

A problem encountered with *E. coli* based expression systems is the difficulty of producing material which is acceptable for therapeutic use. The use of complex media, antibiotic selection and potentially hazardous inducers such as IPTG may potentially render products such as recombinant antibody fragments produced by *E. coli* fermentation technology unacceptable to the regulatory authorities for clinical applications. Evidence demonstrating clearance of these agents from the final product must be provided in order to secure regulatory clearance. Clearance of these agents, and especially demonstrating such clearance, is expensive. It is therefore desirable that an expression system should avoid the three above-mentioned problems.

Avoidance of these problems is not straightforward. Plasmids, especially expression vectors, place a metabolic load on the host cell which acts as a selective pressure favouring loss of the plasmid from the cell. Therefore, in order to reduce the possibility of plasmid loss, or rearrangement of the plasmid to delete the expression activity, it is apparent that the metabolic load placed on a cell by other sources should be reduced to a minimum. Therefore, the use of complex media which contain, in addition to essential amino acids and minerals, a variety of naturally-sourced vitamins, cofactors and the like which alleviate the metabolic load on the cell is favoured.

The term "complex medium" is used herein according to its well-known signification in the art, that is to denote a medium the exact formulation and chemical composition of which has not been determined. Frequently, such media are at least partly derived from natural sources. For example, it is well known to include bovine serum preparations containing a variety of uncharacterised vitamins, growth factors and the like in cell culture media. In contrast, a defined medium is a medium which has been formulated from pure ingredients each of which is known, the medium therefore having a defined formula.

The use of a complex medium introduces the possibility of inclusion of a variety of agents derived from the natural source of certain medium components of which the regulatory authorities will require proof of clearance. Switching to the use of defined media would facilitate obtaining regulatory approval because it can be stated with certainty that the potentially harmful agents are absent from the cell culture. However, the efficiency of protein expression would also be reduced because the metabolic load on the cells in culture may be increased and plasmid expression systems may therefore be destabilised.

A manufacturer producing therapeutic products in cell culture is therefore faced with deciding which route will prove the most cost-effective. In the commercial production systems of the prior art, which use relatively unstable plasmid systems, the equation has often favoured the use of complex media and subsequent clearance demonstration.

The situation is similar in respect of antibiotics. These are commonly used to select against plasmid loss by inclusion of an antibiotic resistance gene on the plasmid. In the absence of antibiotic selection, the increased metabolic load placed on the cell by the plasmid acts to favour growth of plasmid free cells. Therefore, culture of transformed cells without antibiotic is not economic because, even though clearance of the antibiotic does not need to be demonstrated, the potential loss of plasmid from the cells may greatly reduce the efficiency of the expression system.

It should be borne in mind that it is not necessarily the cost of clearing the suspect agent from the product which is high, but rather the cost of providing evidence of this clearance. Thus, for example, IPTG may clear by degradation from the medium, but the cost of demonstrating the clearance of it and potential contaminants and degradation products thereof remains substantial.

It follows, therefore, that it would be desirable to be able to express proteins in a bacterial system in a defined medium in the absence of antibiotic selection and unacceptable inducers such as IPTG. However, due to the problems of plasmid instability, this aim has not been achieved in commercial expression systems of the prior art.

For example, a recent report describing expression of antibody fragments in *E. coli* host cells employs the antibiotic tetracycline to prevent plasmid loss from the cells (Carter et al. BioTechnology 10, 163–167, 1992). Carter et al employ an inducible expression system to prevent heterologous protein expression during host cell growth. Selective advantage for growth of plasmid free cells potentially enhanced by the use of defined medium is avoided by the use of tetracycline to select against such cells.

However, the use of antibiotic is required both during growth, evidently because the vector being used is not sufficiently stable, and during the expression phase. Although this system has the advantage that no inducer need be added, the requirement for antibiotic is not removed, as evidenced by the use of tetracycline in the expression system described. Therefore, the method of Carter et al will require the demonstration of clearance of antibiotic from the final product. This is hypothesised to be necessary because the expression vector used by Carter et al is not sufficiently stable to be cultured in the absence of antibiotic.

Antibodies and antibody fragments, especially recombinant or humanised derivatives thereof, are a class of proteins which it would be extremely desirable to be able to produce by recombinant DNA technology. By humanised antibodies, it is intended to refer to antibodies in which the constant regions are derived from human immunoglobulins, while at least the complementarity determining regions (CDRs) of the variable domains are derived from murine monoclonal immunoglobulins.

A number of improvements over natural immunoglobulins have been documented in the literature, which can only he put into practice by recombinant DNA technology. For instance, the production of CDR-grafted antibodies having CDRs from murine antibodies coupled to human framework regions can only be undertaken using a recombinant expression system. Furthermore, such systems are extremely useful for the production of antibody fragments which are not readily obtained by proteolytic cleavage, such as Fv fragments, and antibody fusions comprising an effector or reporter molecule attached to the antigen binding molecule.

Recombinant antibody fragments whether they be entire antibodies, Fab, Fab', $F(ab')_2$ or Fv fragments, consist of heavy and light chain dimers. A recombinant expression system should therefore be capable of expressing both heavy and light chain genes in such a manner as to render the individual peptides capable of self-assembly into the final product. This has been a stumbling block for recombinant antibody production, and indeed attempts have been made to solve the problem. An example of this is the production of "single chain" Fv fragments, wherein the heavy and light chain polypeptides are physically joined together by a flexible linker group. These molecules avoid the problems of chain association between free heavy and light chain polypeptides.

This system is not necessary, however, for the production of antibody fragments such as Fabs, which comprise heavy and light constant region chains as well as heavy and light variable region chains. For such applications it is desirable to express heavy and light chains separately in the same cell.

In order to facilitate correct assembly of heavy and light chains of antibody fragments, it is preferable to employ an expression system in which the chains are secreted into the culture medium rather than precipitated into the cell as inclusion bodies.

The use of *E. coli* signal sequences fused to polypeptides in order to facilitate their secretion by *E. coli* is known. However, it is apparent in a number of cases that secretion of heterologous proteins is even more deleterious for *E. coli* than accumulation of such proteins intracellularly. Accordingly, it has been found necessary to control the expression of heavy and light chain genes in order to achieve high cell growth and plasmid stability during the growth phase of a bacterial culture.

SUMMARY OF THE INVENTION

The present invention solves the above problems by the provision of a method for the expression of recombinant molecules such as antibody molecules in bacterial hosts in a defined medium in the absence of antibiotic selection. Furthermore, the method of the invention uses an expression vector comprising a regulatable promoter by which the production of foreign proteins may be controlled during the growth phase of the culture, an origin of replication maintaining medium vector copy number and a transcriptional terminator. An example of such a plasmid system is described in International Patent Application No. WO 92/01059 where the vector was used to express antibody fragments. In accordance with the teaching of the art, the host cell transformed with the vector was cultured in the presence of antibiotics. We have now most unexpectedly found that host cells transformed with vectors of this type may, in fact, be cultured in the absence of antibiotic selection.

According to a first aspect the invention provides a method for producing one or more heterologous protein(s) in a bacterial host cell comprising culturing a bacterial host cell transformed with one or more expression vector(s) comprising one or more heterologous DNA sequences under the control of at least one regulatable promoter, an origin of replication maintaining medium vector copy number and a transcriptional terminator characterised in that said host cell is cultured in a defined medium in the absence of antibiotic selection.

The expression vectors for use according to the method of the invention will characteristically show 100% structural stability as determined by running restriction digests of plasmid preparations made from cell samples taken throughout fermentation up to and including harvester; and will characteristically show segregational stability as demonstrated by >80% of the cell population maintaining antibiotic selection marker in defined medium with no antibiotic selection at the point of induction and product expression.

The regulatable promoter is a promoter which tightly represses expression of heterologous DNA during the growth phase of the culture and from which expression preferably may be achieved without addition of chemical inducers such as IPTG.

The expression vector preferably further comprises a gene encoding a repressor which acts on the regulatable promoter to prevent expression of the heterologous DNA sequence(s).

A novel induction system for use with such regulatable promoters is described in our copending International patent application filed on even date herewith and derived from British patent application number 9215550.6 filed on Jul. 22, 1992. The regulatable promoter is therefore preferably repressed by a mature endogenous cellular repressor in a defined medium under conditions such that the inducible promoter is repressed, and expression therefrom is induced by increasing the metabolic rate of the host cell thereby depleting the levels of the mature endogenous cellular repressor. Preferably the increase in metabolic rate is brought about by a switch in carbon source such as from glycerol to glucose.

In a preferred embodiment the invention provides a method for producing a heterologous protein in a bacterial host cell comprising culturing a bacterial host cell transformed with an expression vector comprising a heterologous DNA sequence under the control of a regulatable promoter, an origin of replication maintaining medium vector copy number and a transcriptional terminator characterised in that said host cell is cultured in a defined medium in the absence of antibiotic selection.

The heterologous DNA sequences may code for any eukaryotic polypeptide such as for example a mammalian polypeptide such as an enzyme e.g. chymosin or gastric lipase; an enzyme inhibitor e.g. TIMP; a hormone e.g. growth hormone; a lymphokine e.g. an interferon or interleukin; a plasminogen activator e.g. tPA.

The heterologous DNA sequence(s) will preferably each be fused to a DNA sequence encoding a secretion sequence said secretion sequence being under the control of a regulatable promoter.

The heterologous DNA sequence(s) will preferably encode antibody molecules and fragments thereof and may therefore be gene(s) coding for all or part of an antibody heavy chain and/or light chain.

The antibody fragments may comprise natural antibody fragments, chimeric antibody fragments (the variable domains derived from one species and class of antibody and remaining Ig sequences derived from another species or class of Ig), altered antibody fragments (variable Ig domains plus an additional polypeptide sequence having a different, non Ig function, such as an enzyme or toxin), humanised antibody fragments and engineered antibody fragments (wherein the Ig amino acid sequence has been altered from the natural sequence, e.g. by site-directed mutagenesis, with a view to altering a characteristic of the molecule, e.g. antigen binding specificity or affinity, for example as described in Roberts et al., Nature, 328, 731–734, 1987). The antibody fragments may comprise suitable combinations of the above types of antibody fragment.

Preferably the antibody molecule is a humanised antibody molecule coupling at least the CDRs of a non-human antibody attached to the framework of a human antibody.

Preferably, the antibody molecule is an antibody fragment. For example, the antibody molecule may be a Fab, Fab', $(Fab')_2$ or Fv fragment. Advantageously, it is an Fab' fragment.

The antibody fragments may have any desired antigen specificity. For example, the antibody fragments may have specificity for a cell-specific antigen, such as a tumour antigen, T cell marker, etc. Particularly preferred are antibody fragments which have specificity for tumour-associated antigens such as CEA and TAG72. Chimeric A5B7 antibodies and antibody fragments are described in our copending International patent application WO92/01059. Also preferred are antibodies having specificity to the epitope recognised by murine monoclonal antibody A33 as described in our copending British patent application number 9225853.2 filed Dec. 10, 1992. Particularly preferred are humanised and chimeric forms of A33, and especially preferred are Fab' fragments thereof.

The antibodies may be site-specific antibodies such as tumour-specific or cell surface-specific antibodies, suitable for use in in vivo therapy or diagnosis, e.g. tumour imaging. Examples of cell surface-specific antibodies are anti-T cell antibodies, such as anti-CD3, and CD4 and adhesion molecules, such as CR3, ICAM and ELAM. The antibodies may have specificity for interleukins (including lymphokines, growth factors and stimulating factors), hormones and other biologically active compounds, and receptors for any of these. For example, the antibodies may have specificity for any of the following: Interferons $\alpha$, $\beta$, $\gamma$ or $\delta$, IL1, IL2, IL3 or IL4, etc., TNF, GCSF, GMCSF, EPO, hGH, or insulin, etc.

Preferably, the copy number of the expression vector is between 6 and 50. Advantageously, it is between 10 and 20 and most preferably it is 15.

According to a preferred embodiment of the first aspect of the invention, therefore, there is provided a method for producing antibody molecules or fragments thereof comprising culturing a bacterial host cell transformed with an expression vector comprising a heterologous DNA sequence coding for all or part of a heavy chain and a light chain under the control of a regulatable promoter, an origin of replication maintaining medium copy number and a transcriptional terminator characterised in that said host cell is cultured in a defined medium in the absence of antibiotic selection.

The heterologous DNA sequence coding for all or part of a heavy and a light chain will conveniently be under the control of one regulatable promoter. In some instances it may, however, be possible to place each of the heavy and light chain genes under the control of a separate regulatable promoter, which may be the same or different. Heavy and light chains may also be encoded on separate vectors which are co-transformed and expressed as described in UK Patent No. 2137631B.

Preferably the heavy chain and light chain genes are each fused to a DNA sequence encoding a secretion sequence which may be under the control of the regulatable promoter.

The use of an origin of replication which avoids the single-stranded state during DNA replication has been found to be particularly advantageous in stabilising the plasmid under conditions of high metabolic load. It is hypothesised that, although the metabolic load induced by the plasmid itself is not lowered, the avoidance of the single-stranded state allows the plasmid to replicate more safely, reducing the probability of attack by cellular nucleases or other degrading agents.

Preferably, the medium copy-number origin of replication allows plasmid replication without passing through a single stranded DNA phase.

Preferably, the origin of replication is derived from pSC101 Hashimoto et al (Gene 16 227–235 (1981)) which is a medium copy number plasmid which does not replicate through a single-stranded phase. Preferably, the regulatable promoter/inducer system selected will be one regulation of which is by means of a a clinically acceptable inducer of which clearance demonstration will not be required by the regulatory authorities.

Preferably, the regulatable promoter is the tac promoter and the repressor is the $lacI^Q$ repressor. The advantage of using the $lacI^Q$ repressor is that lactose may be used to induce expression from the tac promoter by inactivating the repressor. This is desirable since lactose is likely to be a clinically acceptable inducing agent.

An antibiotic resistance gene is included in order to allow the application of selective pressure during the growth of the bacteria in order to select for plasmid retention. The inclusion of an antibiotic resistance gene is essential in order to allow for selection during construction of the plasmid. During the expression phase, no antibiotic is added, since the use of antibiotics is undesirable from a clinical and regulatory point of view.

A further advantage of this system is that whereas it is, at present, acceptable to demonstrate clearance of certain substances in order to comply with regulatory requirements, in future it may become strongly discouraged to use such substances at all. Therefore an expression system capable of operating in antibiotic-free defined media may become essential for the production of therapeutic material.

According to a further aspect of the invention, the vector for use in the method of the invention preferably comprises heavy chain and light chain genes arranged with the light chain gene located closer to the promoter such that it is transcribed first. It has been observed that by placing the light chain gene closer to the promoter, in such a manner that it is translationally coupled to the gene which the promoter is directly coupled to, and placing the heavy chain gene downstream from the light chain gene in such a manner that it does not benefit from translational coupling, both cell viability and efficiency of antibody secretion are enhanced.

In order to effect translational coupling, the natural coding sequence of the bacterial gene whose promoter is being used in the expression vector is altered in order to introduce a stop codon just before the beginning of the sequence of the inserted heterologous gene. It is hypothesized that this causes ribosomes, which are efficiently assembled on the mRNA of the bacterial coding sequence, to become disengaged in the close proximity of the translational start site of the heterologous mRNA. This favours the reassembly of the ribosomes on the heterologous mRNA, thus increasing the level of expression.

It is postulated that expression of an excess of heavy chains is deleterious to the host cell. However, arranging the light chain gene such that expression of light chain is favoured ensures an excess of light chains in the cell, thus avoiding the problems associated with excess heavy chain production. The arrangement of cistrons described is designed to favour the expression of an excess of light chains.

In a preferred embodiment of the vector for use in the method of the invention, the vector includes a secretion sequence to effect secretion of antibody heavy and/or light chains. The use of *E. coli* ompA secretion sequences is especially preferred Preferably, the ompA translation initiation signals are also included.

Advantageously, the ompA-antibody light chain fusion is translationally coupled to the lacZ peptide translated from the tac promoter. This may require the alteration of the ompA translation initiation sequence to introduce a stop codon.

Preferably, secretion of the antibody chains from the host cells is carried out at 30° C. It has been found that more protein is secreted at 30° C. than at 37° C., presumably because at the lower temperature the protein is more likely to adopt a translocation-competent state before secretion, or to remain soluble after secretion.

Preferably, the bacterial host cell is a gram-negative bacterial host cell. Preferably, the host cell is an *E. coli* cell.

The expression vectors are preferably based on vectors disclosed in International patent application WO92/01059, and are preferably pACtac derivatives.

Examples of chemically defined medium are provided in Pirt S J (1975) "Principles of Microbe and Cell Cultivation", Blackwell Scientific Publications. Further examples of chemically defined medium are provided in the examples included herein.

BRIEF DESCRIPTION OF THE DRAWINGS

The invention is now described by way of example only with reference to the following figures, in which:

FIG. 5 is an immunoblot comparing the performance of two different strains of bacteria transformed with a vector according to the invention;

DETAILED DESCRIPTION OF THE INVENTION

Experimental

Construction of Heavy and Light-Chain Fusions

Plasmid pQ9kan was constructed by reorganisation of the commercially available vector pTTQ9 (Amersham International plc). pTTQ9 was digested with Sca I, which cuts within the ampicillin resistance gene. A 1.3 kb Hinc II fragment encoding the kanamycin resistance gene was isolated from pUC4K (Pharmacia LKB) and ligated into Sca I cut pTTQ9. Clones with the kanamycin resistance gene inserted in the correct orientation were isolated, and are referred to as pQ9Kan.

A5B7 heavy and light chain sequences cLc (chimeric light chain) and cFd' (chimeric Fd' heavy chain fragment) were isolated as described in International patent application WO 92/01059. These were fused to the *E. coli* secretion sequence ompA and termed ompA-cLc and ompA-cFd', as described in International patent application WO 92101059. The sequences were inserted into pSK (Stratagene) as described in WO 92/01059 to produce pSKompA-cLc and pSKompA-cFd'.

Insertion of ompA-cLc and ompA-cFd' into pQ9Kan was carried out by digesting pQ9Kan with Sal I and Eco RI and inserting the required sequence isolated from pSKompA-cLc or pSKompA-cFd' as required, as Xho I-Eco RI fragments, to give pQ9Kan-cLc and pQ9Kan-cFd'. To form pQ9Kan-cLc-cFd', pQ9Kan-cLc was digested with Eco RI. The protruding 5' tail was filled in with T4 DNA polymerase to form a blunt end. The ompA-cFd' gene was isolated as an Xho I-Eco RI fragment from pSKompA-cFd', and filled in similarly. Ligation of the two filled in products and subsequent selection for the desired orientation of insertion yielded pQ9Kan-cLc-cFd'.

pQ9Kan-cFd'-cLc was constructed in an analogous fashion from pQ9Kan-cFd' Eco RI (filled) and the ompA-cLc gene digested with Eco RI and Xho I, and filled in.

Expression of Chimeric A5B7 Fab' in pQ9kan

Figure 1:
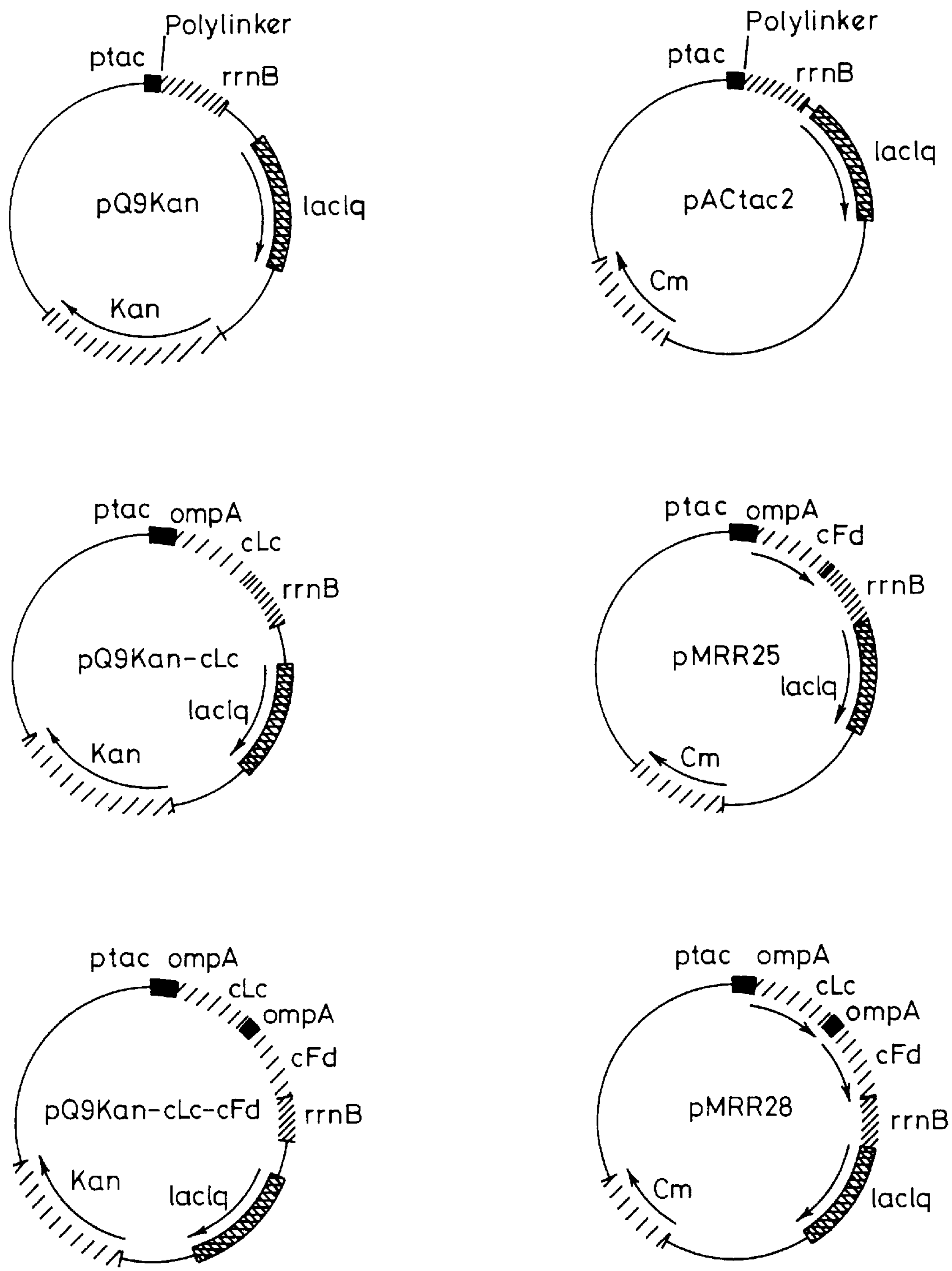
FIG. 1 is a diagrammatic representation of the vectors of the invention and intermediates used in their preparation.
Figure 2:
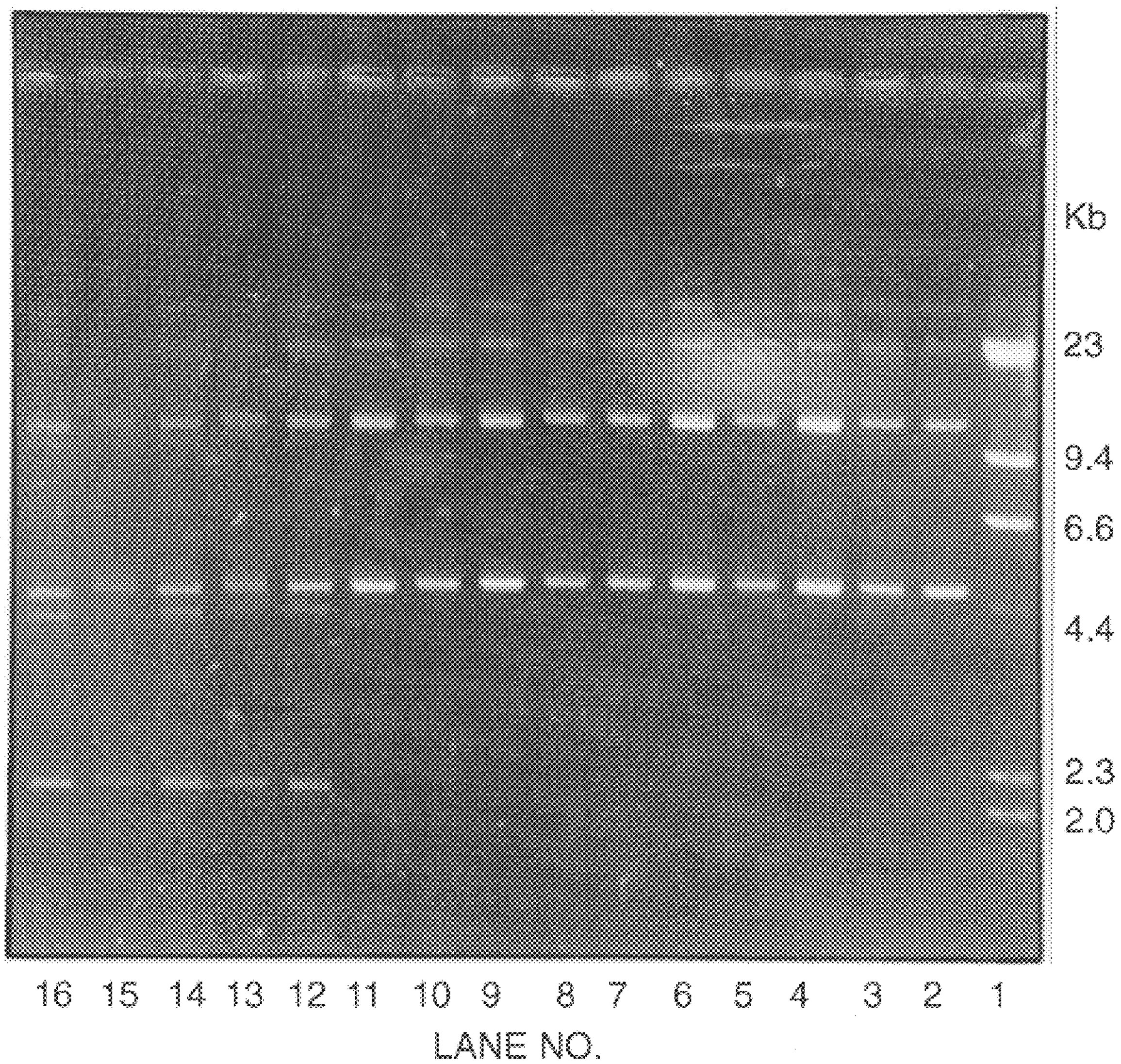
FIG. 2 is a photograph of an agarose gel electrophoresis experiment of plasmid preparations derived from bacterial cultures transfected with plasmids comprising heavy and light chain genes in the order cLc-cFd' and cFd'-cLc.

Expression and stability studies were performed with plasmids pQ9Kan-cLc-cFd' and pQ9Kan-cFd'-cLc in *E. coli* strains XL1 Blue and W3110, in both shake flasks and 2 l fermentors. A map of the former is shown in FIG. 1, and the latter is identical except for the relative positions of ompA-cLc and ompA-cFd' fusions with respect to the tac promoter. In shake flask experiments both plasmids displayed serious segregational instability in XL1Blue, even in non-inducing conditions with kanamycin present. In W3110 pQ9Kan-cFd'-cLc appeared somewhat less segregationally unstable but nevertheless showed serious and progressive plasmid loss (see FIG. 2). FIG. 2 is an Agarose gel showing preparations of pQ9Kan-cLc-cFd' and pQ9Kan-cFd'-cLc plasmids. Lane 1: λ-Hind III markers; lanes 2 to 11: plasmid preparations from strain W3110 transformed with pQ9Kan-cLc-cFd' (A5B7); lanes 12 to 16: plasmid preparations from strain W3110 transformed with pQ9Kan-cFd'-cLc (A5B7).

In lanes 2 to 11, the intact plasmid can be seen just above the 4.4 Kb marker and no degradation products are apparent. In lanes 12 to 16, on the other hand, degradation products may be seen at about 2.1 and 4 Kb.

W3110/pQ9Kan-cLc-cFd' proved the most stable strain/plasmid combination, an approximately constant proportion (50%) of the cells retaining the plasmid in non-inducing conditions. This strain, however, consistently failed to grow in fermentors, and unlike the other three strains also consistently failed to grow beyond OD600 of 10 in shake flask cultures. In structural stability studies in fermentors on the other three strains pQ9Kan-cFd'-cLc was observed to suffer deletions in both strains in non-inducing conditions, while pQ9Kan-cLc-cFd' appeared structurally stable in XL1Blue.

It was concluded that the promoter-cLc-cFd' order gives better structural stability than the promoter-cFd'-cLc order, and that only the W3110/pQ9Kan-cLc-cFd' combination was sufficiently stable for expression experiments to the meaningful. When shake flask cultures of this strain were induced at an OD600 of 5, Western immunoblotting revealed the presence of two immunoreacting bands roughly of the size expected of Fab' fragments in cell extracts but not in culture supernatants. Optimisation of induction times and feeding of nutrients after induction improved the yield of this material in cell extracts and led to its appearance in culture supernatants. Rough estimates of yield by comparison on immunoblots with measured amounts of chimeric Fab' made in CHO cells suggested a yield of about 5 mgs/l in these culture supematants. Because this strain was unable to grow in fermentors expression constructs were made and tested using other vectors.

Expression of Chimeric A5B7 Fab' in pACtac pACtac is a medium copy number (approx 15/cell) relative of pQ9kan. It was constructed by replacing the kanamycin selectable marker and pUC replication functions of the latter with those of pACYC184 (see FIG. 1) as described in International patent application WO 92/01059. The plasmids pSKompA-cLc and pSKompA-cFd' contain the A5B7 chimeric light and heavy chains respectively fused precisely to the ompA signal sequence as described above, inserted into pSK.

The ompA-cic and ompA-cFd' fusions were isolated as Xhol-Sma1 fragments and from pSKompA-cLc and pSKompA-cFd' respectively and cloned into the Sal1-Pvull gap of pSP73 (Promega Corp.) to give plasmids pMMR026 and pMRR027 respectively, this to allow subsequent manipulation as EcoR1 fragments. The EcoR1 fragment of pMRR027 carrying the ompA-cFd' fusion was then cloned into pMRR024 (see WO 92/01059), partially cleaved with EcoR1 to give pMRR028 (see FIG. 1), which thus carried the Fab' genes in the order promoter-cLc-cFd'. pMRR028 was transformed into strains W3110 and XL1Blue. Expression studies were carried out first on XL1Blue (pMRR028) to provide a direct comparison with results for the two plasmid system.

Figure 3:
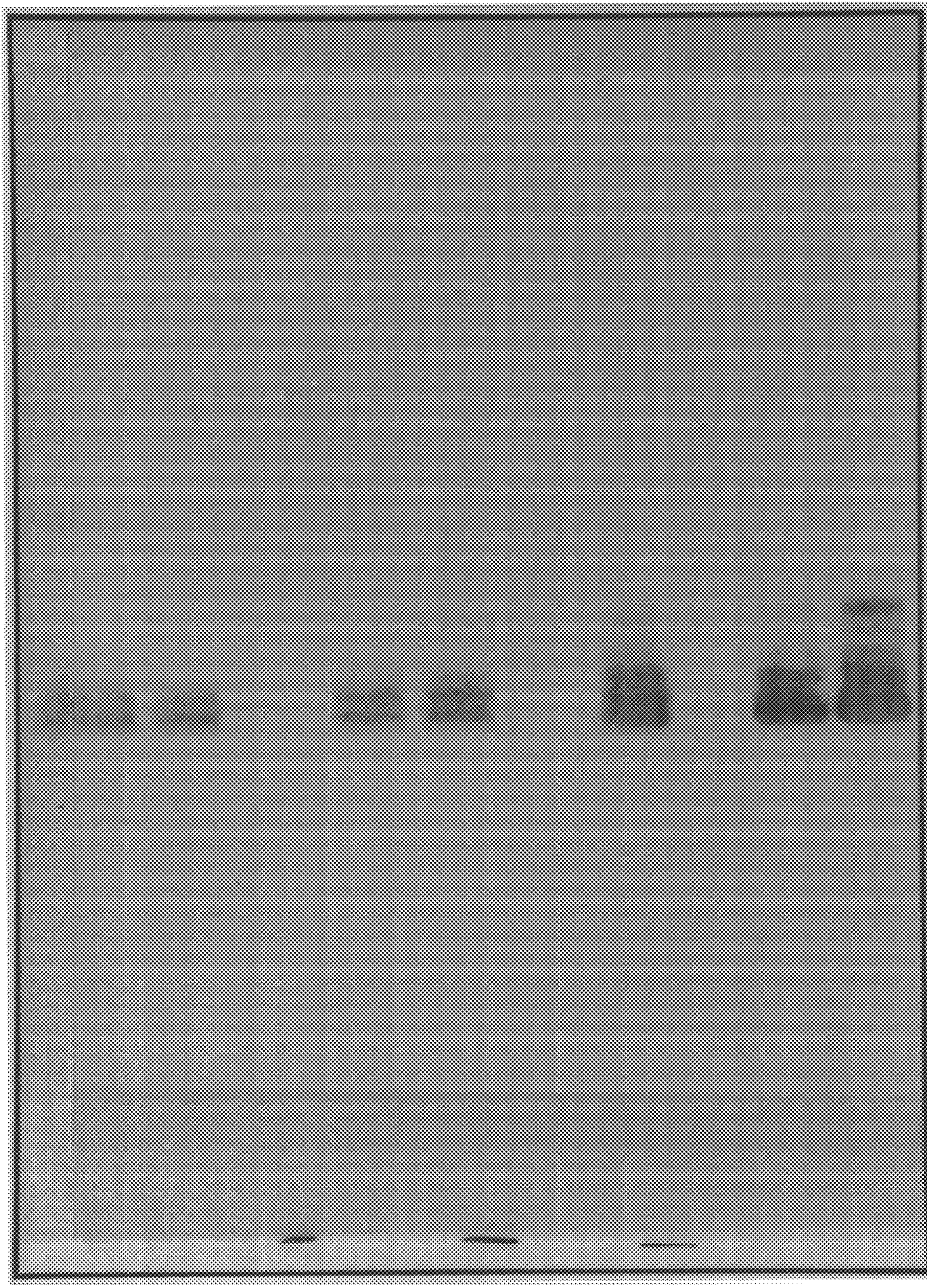
FIG. 3 is an immunoblot of cultures of bacteria transformed with vectors according to the invention.

Shake flask cultures of XL1Blue (pMRR028) in YEGLY medium plus chloramphenicol were induced at an OD600 of 10 with 200 μM IPTG. Western immunoblotting of culture supernatants along with a series of measured amounts of purified chimeric A5B7 Fab's suggested a yield in excess of 30 mg/l. As FIG. 3 shows no Fab' was detected in cell extracts of uninduced cultures, suggesting extremely tight regulation of expression for this strain. Structural and segregational stability tests showed no sign of instability through the six or seven generations in YEGLY medium plus chloramphenicol examined in these experiments for either induced or uninduced cultures.

FIG. 3 is an Immunoblot of samples from shake flask cultures of strain XL1 Blue (pMRR028).

lane 1 shows a supernatant sample from a fermentation of XL1 Blue (pQ9kan-cLc, pMRR025)

lanes 2, 4 and 5 supernatant samples from induced cultures of XL1 Blue (pMRR028)

lanes 3 and 6 supernatant samples from uninduced cultures of XL1 Blue (pMRR028)

lanes 7, 9 and 10 cell extracts from induced cultures of XL1 Blue (pMRR028)

lane 8 cell extract from an uninduced culture of XL1 Blue (pMRR028)

1.5 l batch fermentations were performed using the same medium and induction conditions for both XL1Blue (pMRR028) and W3110 (pMRR028). Immunoblotting suggested roughly equal yields for both strains.

Figure 4:
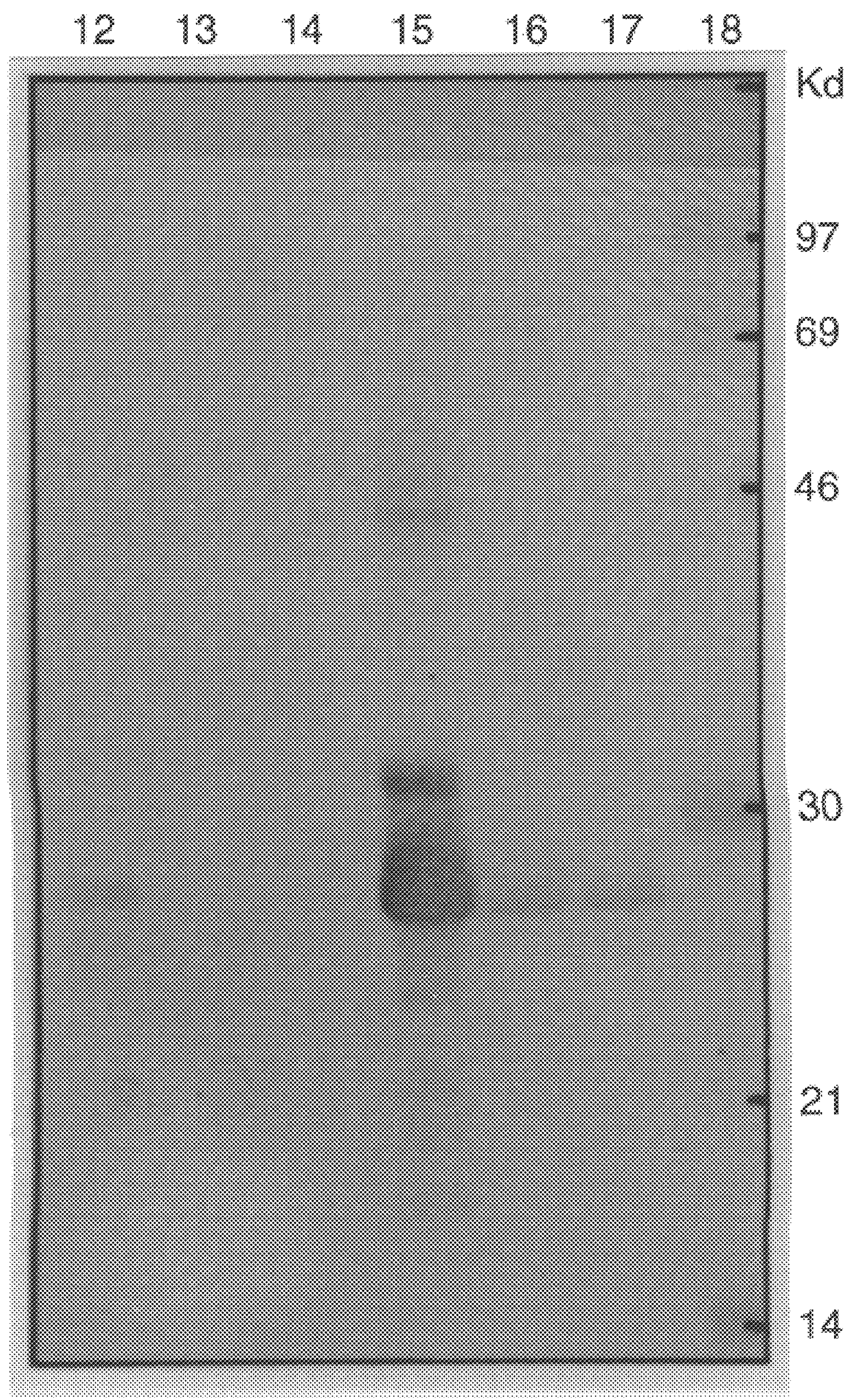
FIG. 4 is a photograph of a western blot which compares the yields of antibody product from dual origin vectors transfected with cLc-cFd' and cFd'-cLc gene constructs.

FIG. 4 is a Western blot of culture supematants and cell extracts from cell lines transformed with DUOV vectors transformed with cLc-cFd' and cFd'-cLc genes.

lane 12 culture supernatant of XL1B transfected with pMRR032 (cLc-cFd');

lanes 13 and 14 culture supernatants of XL1B transfected with pMRR033 (cFd'-cLc).

lane 15 cell extract of XL1B transfected with pMRR032 lanes 16 and 17 cell extract of XL1B transfected with pMRR033. The cLc-cFd' gene order can be seen to give much higher yields of product.

As shown in FIG. 4, however, one very significant difference was observed between the Fab' products appearing in the culture supernatants of XL1Blue and W3110—the latter appeared to be secreting only the normal sized light chain. This immunoblot revealed that the slower migrating form of the light chain is, however, present in the W3110 cell extracts. This suggests selective release of the normal sized light chain by this strain, rather than selective synthesis.

Expression and Fermentation Development Towards a Clinically Acceptable Process

In order to develop a clinically-compatible fermentation process lactose instead of IPTG was used for induction of pMMR028 in W3110. This approach involves the use of defined medium without antibiotic selection, in the production fermentor.

Subculturing experiments in complex medium were performed for W3110 (pMRR028) to assess the segregational and structural stability of the plasmid. No plasmid loss or deletions were observed in this medium over the six to seven generations which are required in the production fermentation (1000 l scale)—see FIG. 5.

Figure 5:
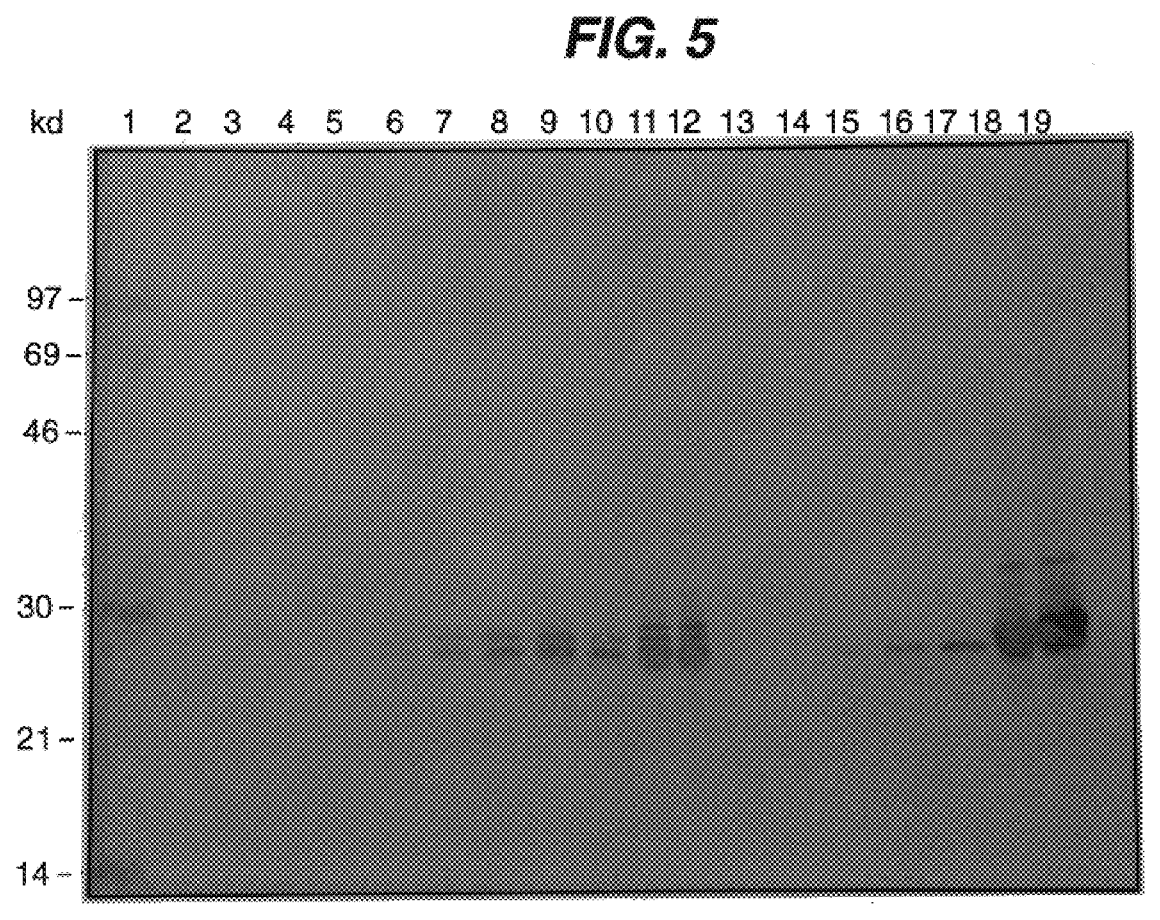

FIG. 5 is an immunoblot of samples from fermentations of XL1 Blue (pMRR028) and W3110 (pMRR028).

lane 1 molecular weight markers lanes 2–10 culture supernatant samples 1–9 from XL1 Blue (pMRR028).

lanes 11 and 12 cell extracts from XL1 Blue (pMRR028) samples 6 and 9 lanes 13–17 culture supernatant samples 1, 3, 5, 7 and 9 from W3110 (pMRR028)

lanes 18 and 19 cell extracts from W3110 samples 6 and 9.

Samples were taken approximately hourly from t=10 hours, with inductions at time of sample 3 for XL1 Blue (pMRR028) and sample 1 for W3110 (pMRR028).

Controlled exponential phase cultures of this strain have been grown in defined minimal salts medium to a cell density (OD600 of >30) approaching that which is required for high yielding production fermentations. Such cultures were successfully induced with IPTG (see FIG. 6) and shown to give yields similar to those observed for YEGLY medium.

Figure 6:
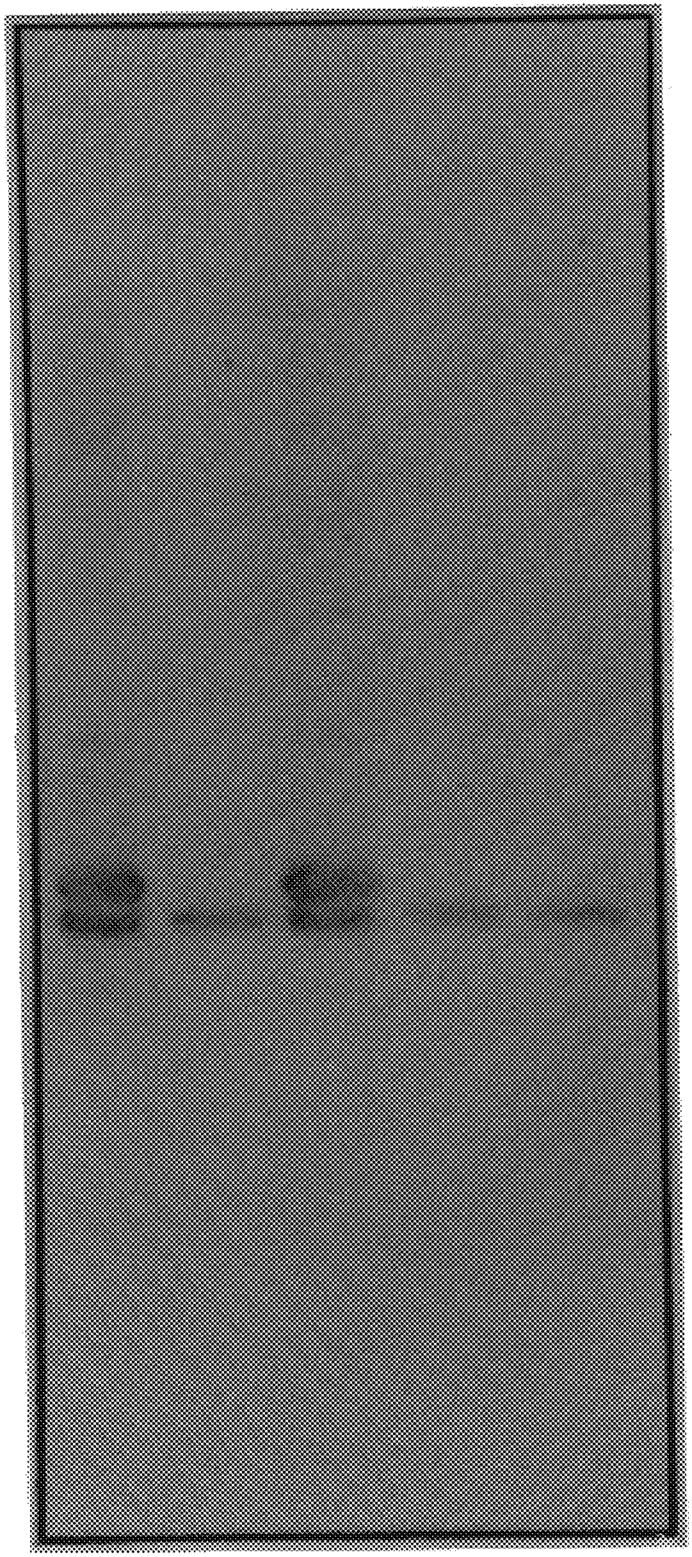
FIG. 6 is an immunoblot showing the performance of host cells transformed with a vector according to the invention in a defined medium.

FIG. 6 is an immunoblot of samples from fermentations of W3110 (pMRR028) in defined medium.

lanes 1 and 3 cell extracts lanes 2, 4 and 5 culture supernatant samples

Figure 7:
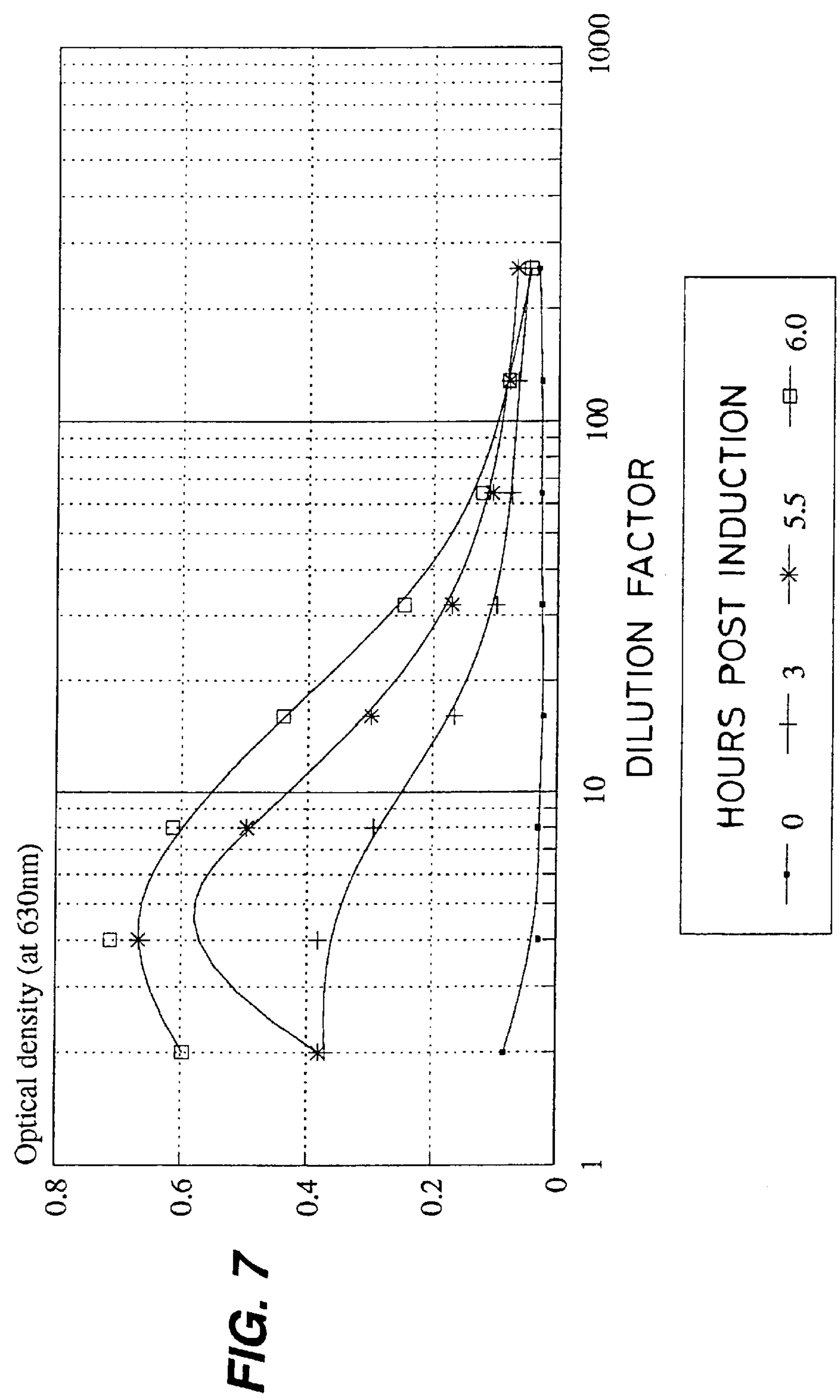
FIG. 7 is a graph of CEA binding assays on crude culture fermentation samples from the defined medium cultures.

CEA binding assays were performed on crude supernatant samples from these fermentations, with the results shown in FIG. 7. As this Figure indicates the supematants contain material active in antigen binding.

Figure 8:
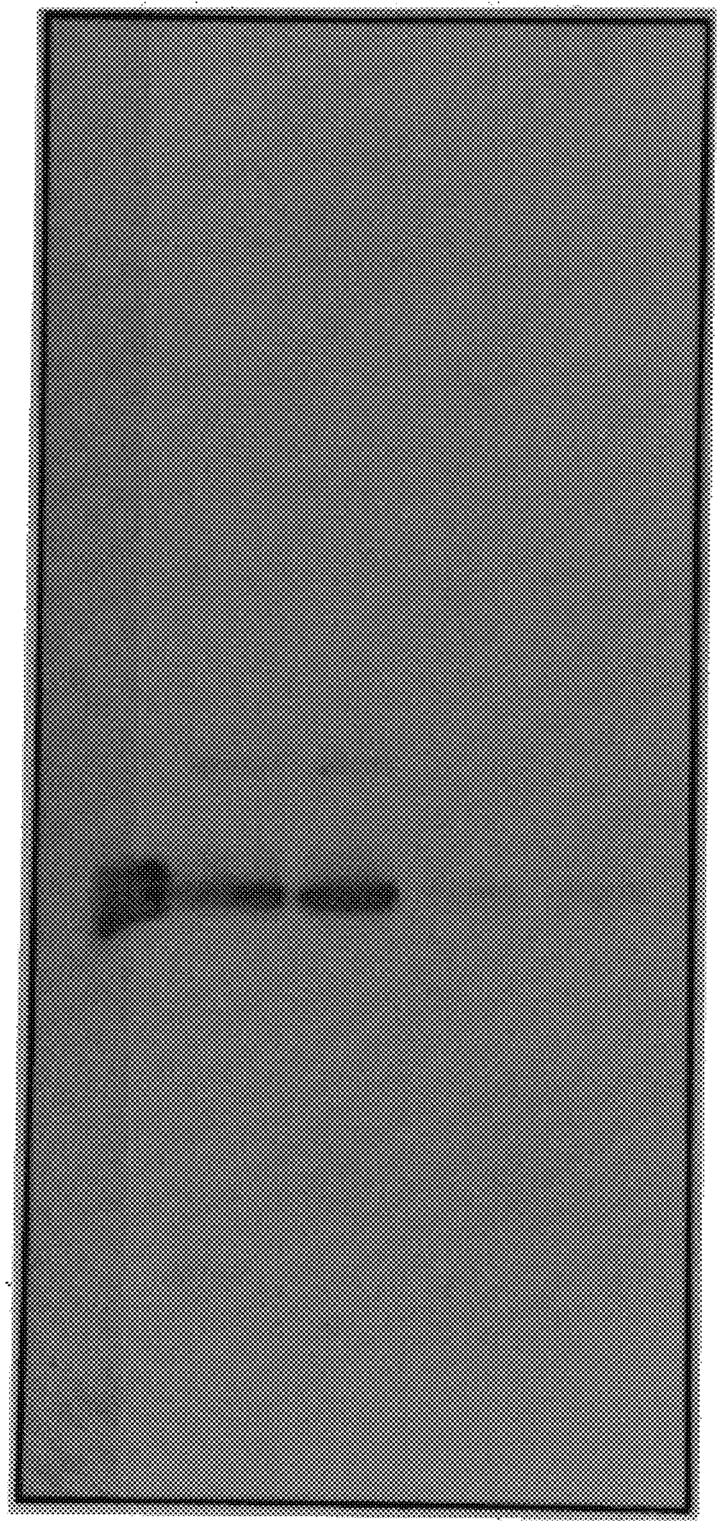
FIG. 8 shows the production of antibody fragments when cultures are induced by lactose.

Induction of Fab' expression for W3110 (pMRR028) growing in YEGLY medium in a 1.5 l fermentor has also been achieved by feeding lactose rather than adding IPTG batchwise. A Western immunoblot of cell extract and supernatant samples from this fermentation is shown in FIG. 8, and suggests relatively low levels of Fab' expression and secretion. Interestingly the cell-bound immunoreacting material shows a much greater proportion of the normal sized light chain than observed with IPTG. Induction appeared to occur late in the fermentation, some 8–10 hours after the start of lactose feeding.

FIG. 8 is an immunoblot of samples from a fermentation of W3110 (pMRR028) in YEGLY medium, with induction by lactose feeding.

lane 1 chimeric A5B7 Fab' standard purified from CHO cells lanes 2 and 3 cell extracts after induction lanes 4 and 5 culture supernatant samples after induction The OUR profile of this fermentation showed an isolated peak around this time which may have represented a switch to utilisation of lactose upon exhaustion of preferred carbon sources, with consequent induction by allolactose.

Figure 9:
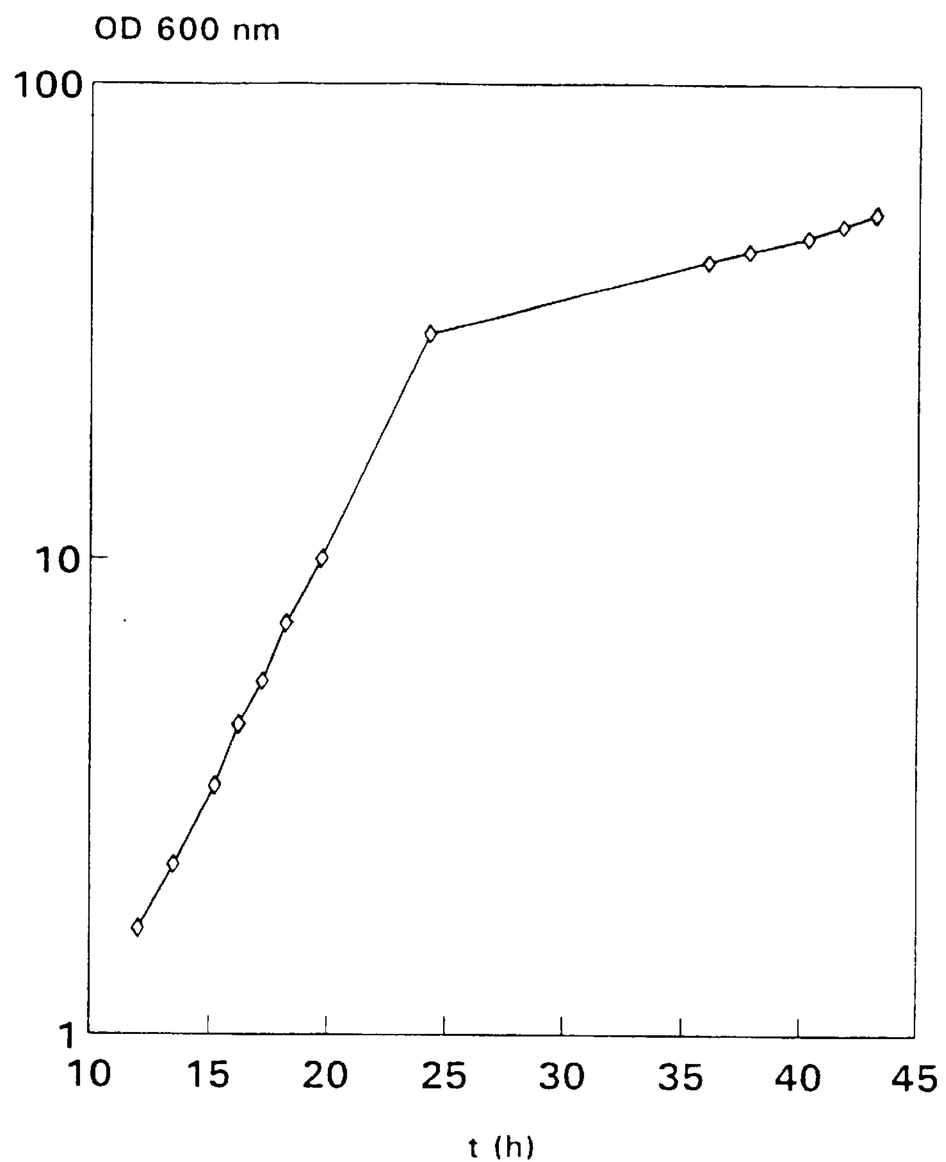
FIG. 9 shows the growth rate of host cells transformed with a vector according to the invention in a defined growth medium with induction of gene expression by lactose feeding.
Figure 10:
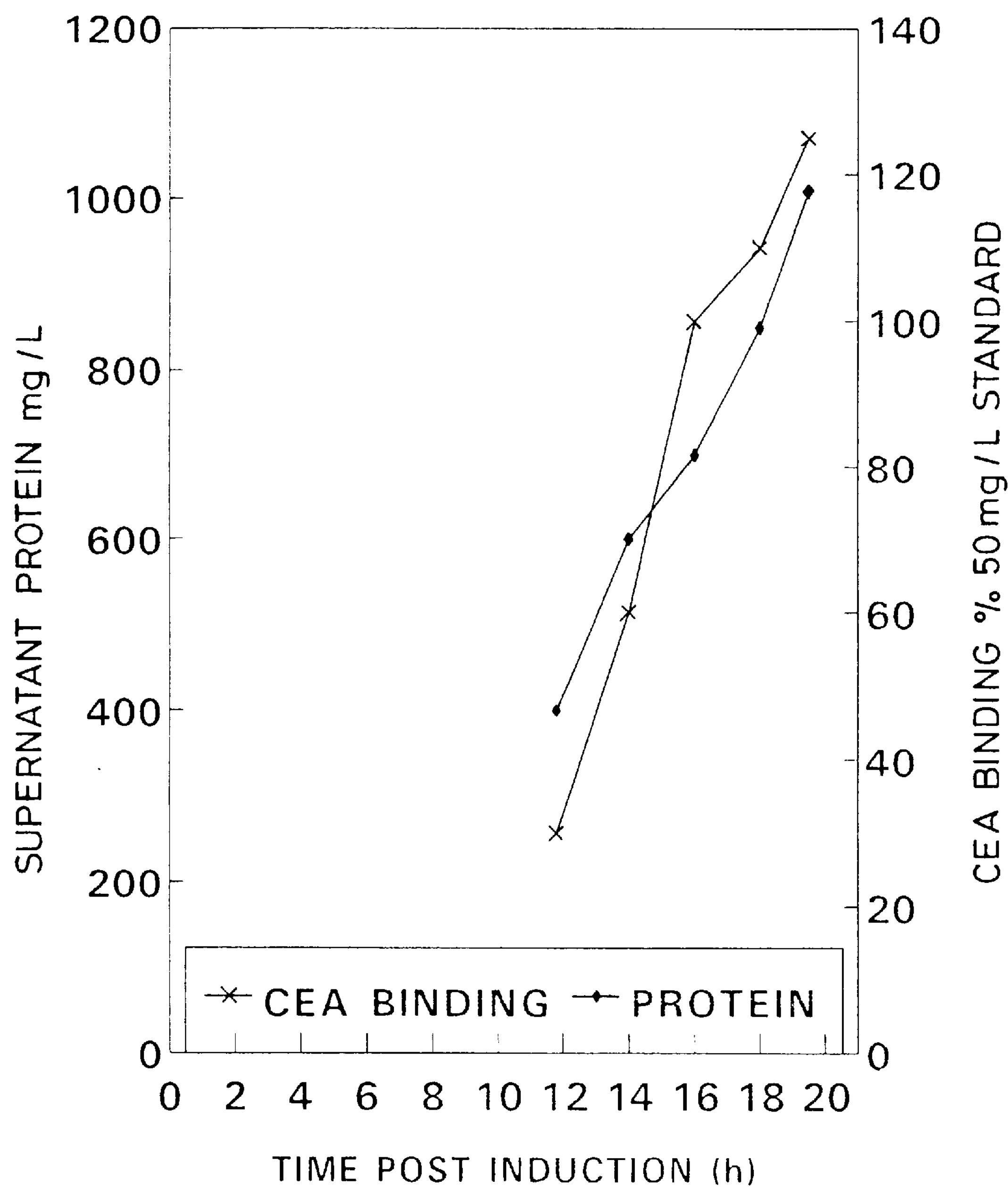
FIG. 10 shows the accumulation profile of Fab' protein produced in the experiment of FIG. 9.

These findings were supported by a subsequent experiment which demonstrated actual expression of A5B7 Fab' in a defined, antibiotic-free medium under lactose induction. Fermentations were performed with strain W3110 carrying pMRR028 in defined medium using glucose as the initial carbon source prior to switching to lactose fed at a rate suitable for achieving induction and for supporting further growth. The growth curve from one such fermentation is given in FIG. 9, which demonstrates diauxic growth. The first growth phase ceased at the point of glucose exhaustion, which occurred at an OD600 of about 30. The specific growth rate in the second phase was lower but continued up to the point of harvest. This lower specific growth rate should allow greater cell concentrations to be kept oxygen sufficient. Accumulation of product, as defined by both Coomassie Blue binding for protein estimation and CEA-binding, is shown in FIG. 10. Accumulation of active Fab' in the medium continued up to the point of harvest. Western immunoblots revealed the same four principal species seen in the culture supernatant for the dual origin system.

Figure 11:
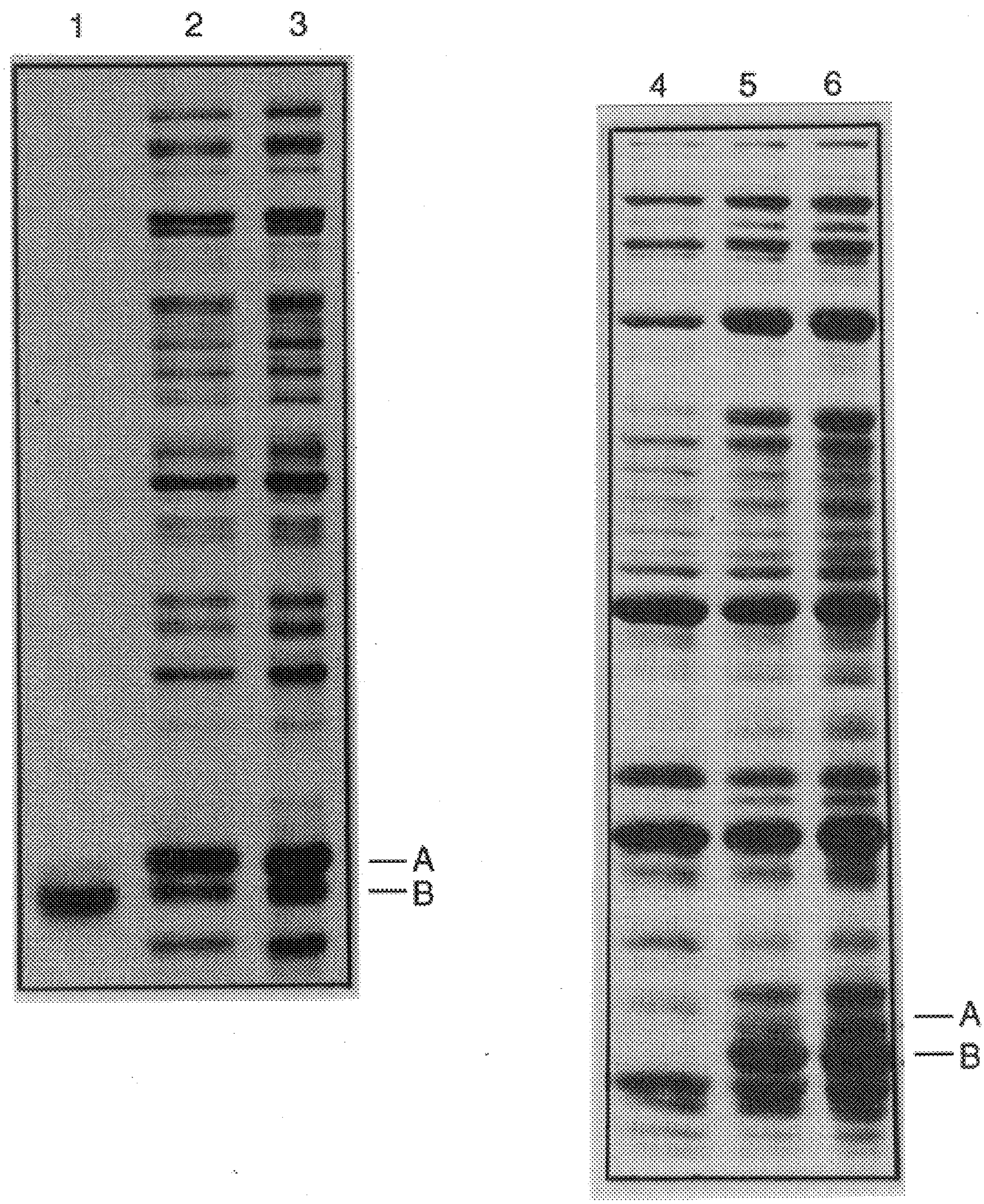
FIG. 11 is a western blot of the extract from the cells grown in the experiment of FIGS. 9 and 10.

Reduced cell extracts of W3110 (pMRR028) showed a single band on immunoblots of SDS-PAGE. This species is 27 kD molecular weight, is the major cell-associated protein in induced cells, is not present in uninduced cells and co-migrates with active Fab' made in mammalian cells (see FIG. 11). FIG. 11 is an SDS-PAGE of *E. coli* W3110 (pMRR028) cell extracts.

Cell extracts were electrophoresed on a 12% reducing gel.

lane 4 before induction;

lanes 2 and 5 4 hours after induction;

lanes 3 and 6 18 hours after induction.

1—cFab' standard from CHO cells. Bands A and B are the two proteins appearing only after induction. Only band B is released into the medium.

It proved possible to observe CEA binding activity in cell lysates from a wide range of fermentations, with titres up to 250 mg Fab'/L of lysate.

EXAMPLE A

Methods for the Expression of A33 Grafted Fab' in *E. coli* Using the pAC tac Expression Vector Humanised A33 Fab' may be constructed and expressed in *E. coli* as described in British patent application number 9225853.2 filed Dec. 10, 1992 and initial British patent application filed on even date herewith (ref. PA 345).

1. Storage of Strains
2. Revival of Cultures and Inoculum Preparation
3. Media
4. Fermentor Culture and Induction Procedures
5. Harvesting
6. Periplasmic Extraction Procedures.

1. STORAGE OF STRAINS

A single colony from a freshly transformed plate was streaked out on an LA chloramphenicol plate. A single colony from this plate was used to inoculate a 250 ml Erlenmeyer flask containing 40 ml LB medium+chloramphenicol. This flask was incubated at 30° C. and 250 RPM in an orbital incubator until the culture reached an optical density (OD 600 nm) of 2 (mid exponential growth phase) taking approximately Bh to reach this point. Aliquots (750 μl) of this culture were mixed with 250 μl sterile glycerol solution (50% v/v in $H_2O$) in a 2 ml sterile ampoule (Sterilin). These glycerol stocks were stored at −70° C. without controlling freezing rate.

Lyophilised stocks were prepared from a similar culture to that described above (from the same original transformant). Sterile sucrose solution rather than glycerol was added as a cryoprotectant (after incubation) to a final concentration of 10% (w/v).

2. REVIVAL OF STRAINS AND INOCULUM PREPARATION

Inocula for all experiments were prepared from frozen glycerol stocks in LB medium containing Cm or Amp as appropriate, the seeding density was usually 300 μl glycerol stock per liter LB. Inoculum cultures, grown in Erlenmeyer flasks (1L containing 200 ml medium) incubated at 30° C. and 250 RPM in an orbital shaker were used when an OD 600 nm of 3 had been attained (normally 12–16 h). Fermentors and shake flasks were seeded with 5–10% volumes of inoculum.

| 3. MEDIA | |
|---|---|
| 3.1 LA: Luria Agar<br>LA Cm: LA + chloramphenicol 25 μg/ml | |
| 3.2 LB: Luria Broth<br>LB Cm: LB + chloramphenicol 25 μg/ml | |
| 3.3 SM6B<br>Component | g/L |
| $(NH_4)_2SO_4$ | 5.0 |
| $NaH_2PO_4$ | 6.24 |
| KCl | 3.87 |
| $MgSO_4.1H_2O$ | 0.56 |
| Citrate | 4.0 |
| SM6A Trace Element solution | 10 ml/L |
| Antifoam (Mazu DF843 10% in $H_2O$) | 1.0 ml/L |
| Made up to 0.2 L with deionised water (5x solution) | |
| SM6B Trace element solution<br>Component | g/L 100x<br>stock solution |
| Citrate | 100.0 |
| $CaCl_2.6H_2O$ | 5.0 |
| $ZnSO_4.4H_2O$ | 2.0 |
| $MnSO_4.4H_2O$ | 2.0 |
| $CuSO_4.5H_2O$ | 0.5 |
| $CoSO_4.6H_2O$ | 0.4 |
| $FeCl_3.6H_2O$ | 9.67 |
| $H_3BO_3$ | 0.03 |
| $NaMoO_4$ | 0.02 |

Made up to 1 l with deionised water. Components were added in the order shown and were allowed to dissolve completely prior to the addition of the next salt.

Medium SM6B was kept as a 5× solution, the concentrated salts solution was added to the fermentor to the correct concentration for the culture volume up to the point of induction (i.e. sterilised volume+inoculum+glucose feeds). Subsequent salt requirements arising from the increase in volume brought about by feeding lactose solution were supplied at the time of lactose feeding. The fermentor was brought up to the correct volume pre sterilisation with deionised water.

Defined media were brought to pH 6.95 using 3.6M $NH_4OH$ after autoclaving in situ at 121° C. for 20 min. After sterilisation of the salts solution, glucose was added to the fermentor as a 50% (w/v) solution to a final concentration of 20 g/L.

Glucose and lactose were autoclaved separately as 50% solution (w/v) in $H_2O$ and added to cultures as described in the fermentation methods section. Prior to autoclaving, conc $H_2SO_4$ (100 μl per liter) was added to glucose solutions.

Casamino acids (Difco, 200 g/l) solution in $H_2O$ sterilised by autoclaving) were added to the fermentor at the start of lactose feeding to give a final accumulated supply of 20 g/L (final fermentor volume).

4. FERMENTATION CONDITIONS

Fermentations were made in medium SM6B, glucose was used as the initial carbon and energy source for all fermentations and was added after medium sterilisation to a concentration of 20 g/l. Culture pH was brought to and maintained at 6.95 by the addition of 3.6M $NH_4OH$ or 2M $H_2SO_4$. Dissolved oxygen tension (DOT) was maintained above 10% air saturation by control of agitator speed (between 250 and 1000 RPM for 2 and 15L fermentations and between 150 and 650 RPM for 150L fermentations) culture temperature was maintained at 30° C. throughout the fermentation. Cultures were aerated at 0.75–1.5 v/v/min. During the later stages of 150L fermentations the vessel was pressurised to 0.4 bar to maintain the DOT above 10%. Oxygen utilisation rates (OUR) and carbon dioxide evolution rates (CER) were determined from exhaust gas analysis values carried out by mass spectrometry. OUR reached maximum values of approx. 150 mmol/l/h in the fermentations described.

Lactose inductions; Induction of product expression was initiated by switching the carbon source to lactose from glucose. Glucose was fed to support the culture to an OD of approximately 40 (an accumulative addition of 40 g/l). Lactose feeding was started at an OD of approximately 35, as with glucose, lactose was fed as individual shots of 60% lactose to a concentration of up to 60 g/l culture when required or as a predetermined exponential feed program.

Cultures induced by lactose feeding were harvested 24 h after the switch from glucose to lactose utilisation.

Where casamino acids were added, these additions were made or started, at the start of lactose feeding.

5. HARVESTING

Fermentors were harvested 24 h after the switch to lactose utilisation. 2L fermentations were clarified by centrifugation 4200 RPM max 250 mm. 15 and 150L fermentations were clarified by tangential flow filtration (TFF) using a Millipore prostack system with durapore 0.65 μm membranes and a retentate flow rate of approx. 10 L/min/channel. Clarification of fermentation broths by TFF was superior to scaleable centrifugation processes.

6. PERIPLASMIC EXTRACTION PROCEDURES

Product was released from the periplasm by incubating culture pellets or concentrated cell suspensions harvested by centrifugation or TFF respectively. Harvested cells were washed in Tris HCl buffer 100 mM pH 7.4 and then incubated in Tris buffer 100 mM pH 7.4 containing 10 mM EDTA. Incubations were made at 40° C. for 4H. Repeated incubations of the cells produced further material.

EXAMPLE B

Methods for the Expression of Antibody Fragments in *E. coli* Using the Dual Origin and pAC tac Expression Vectors 1. Storage of Strains
2. Revival of Cultures and Inoculum Preparation
3. Media
4. Shake Flask Culture and Induction Procedures
   - 4.1 Host strain W3110 with pAC tac vector
   - 4.2 Host strain W3110 with dual origin vector
5. Fermentor Culture and Induction Procedures
   - 5.1 Host strain W3110 with pAC tac vector
   - 5.2 Host strain W3110 with dual origin vector
6. Periplasmic Extraction Procedures

1. STORAGE OF STRAINS

A single colony from a freshly transformed plate was streaked out on an LA plate containing the appropriate antibiotic selection. A single colony from this plate was used to inoculate a 250 ml Erlenmeyer flask containing 40 ml LB medium+appropriate antibiotic selection (dual origin vector: ampicillin, pAC tac vector: chloramphenicol). This flask was incubated at 30° C. and 250 RPM in an orbital incubator until the culture reached an optical density (OD 600 nm) of 2 (mid exponential growth phase) taking approximately 8 h to reach this point.

Aliquots (750 μl) of this culture were mixed with 250 μl sterile glycerol solution (50% v/v in $H_2O$) in a 2 ml sterile ampoule (Sterlin). These glycerol stocks were stored at −70° C. without controlling freezing rate.

2. REVIVAL OF STRAINS AND INOCULUM PREPARATION

Inocula for all experiments were prepared from frozen glycerol stocks in LB medium containing Cm or Amp as appropriate, the seeding density was usually 300 μl glycerol stock per liter LB. Inoculum cultures, grown in Erlenmeyer flasks (1L containing 200 ml medium) incubated at 30° C. and 250 RPM in an orbital shaker were used when an OD 600 nm of 3 had been attained (normally 12–16 h). Fermentors and shake flasks were seeded with 5–10% volumes of inoculum.

| 3. MEDIA | |
|---|---|
| 3.1 LA: Luria Agar | |
| LA Cm: LA + chloramphenicol 25 μg/ml | |
| LA Amp: LA + ampicillin 25 μg/ml | |
| 3.2 LB: Luria Broth | |
| LB Cm and LB Amp both 25 μg/ml | |
| 3.3 YEGLY | |
| Component | g/L |
| Glycerol | 20.0 |
| $(NH_4)_2SO_4$ | 7.0 |
| $NaH_2PO_4.2H_2O$ | 6.24 |
| Yeast extract (Difco) | 40.0 |
| SM6 trace elements | 10 ml/L |
| Antifoam solution (1) % mazu DF843) | 1 ml/L |
| This formulation was made up to 1 L with deionised water. | |
| 3.4 SM6 | |
| Component | g/L |
| $(NH_4)_2SO_4$ | 5 |
| $NaH_2PO_4$ | 6.24 |
| Trace element solution (SM6) | 10 ml/L |
| Antifoam solution (10% mazu DF843) | 1 ml/L |

This formulation was made up to 0.96L with deionised water. Where the carbon source used was glycerol this was added to a concentration of 20 g/L prior to autoclaving. Where glucose and or lactose were used these were added post sterilisation as 50% solutions (sterilised by autoclaving) to final concentrations of 20 g/L.

| SM6 Trace element solution Component | g/L 100x stock solution |
|---|---|
| NaOH | 15.0 |
| EDTA | 60.0 |
| $MgSO_4.7H_2O$ | 20.0 |
| $CaCl_2.6H_2O$ | 5.0 |
| $ZnSO_4.4H_2O$ | 2.0 |
| $MnSO_4.4H_2O$ | 2.0 |
| $CuSO_4.5H_2O$ | 0.5 |
| $CoCl_2.6H_2O$ | 0.095 |
| $FeSO_4.7H_2O$ | 10.0 |
| $H_3BO_3$ | 0.031 |
| $Na_2MoO_4$ | 0.002 |

Each component was dissolved individually in deionised water and added to the bulk solution in the sequence shown to a final volume of 1L.

| 3.5 SM6A Component | g/L |
|---|---|
| $(NH_4)SO_4$ | 5.0 |
| $NaH_2PO_4$ | 6.24 |
| KCl | 3.87 |
| $MgSO_4.1H_2O$ | 0.56 |
| Citrate | 4.0 |
| SM6A Trace Element solution | 10 ml/L |
| Antifoam (Mazu DF843 10% in $H_2O$) | 1.0 ml/L |

Made up to 0.95L with deionised water.

| SM6A Trace element solution Component | g/L 100x stock solution |
|---|---|
| Citrate | 100.0 |
| $CaCl_2.6H_2O$ | 5.0 |
| $ZnSO_4.4H_2O$ | 2.0 |
| $MnSO_4.4H_2O$ | 2.0 |
| $CuSO_4.5H_2O$ | 0.5 |
| $CoSO_4.6H_2O$ | 0.4 |
| $FeCl_3.6H_2O$ | 9.67 |
| $H_3BO_3$ | 0.03 |
| $NaMoO_4$ | 0.02 |
| KCl | 74.5 |

Made up to 1 l with deionised water. Components were added in the order shown and were allowed to dissolve completely prior to the addition of the next salt.

Defined media were brought to pH 6.95 using 3.6M $NH_4OH$ after autoclaving.

Carbon sources for defined media were as described in the fermentation methods section.

All media were sterilised by autoclaving at 121° C. for 20 min.

Glucose and Lactose were autoclaved separately as 50% solutions (w/v) in $H_2O$ and added to cultures as described in the fermentation methods section. Prior to autoclaving, conc $H_2SO_4$ (100 μl per liter) was added to glucose solutions.

Glycerol for feeding during fermentations was autoclaved neat or as a 50% w/v solution in $H_2O$.

Casamino acids (Difco, 200 g/l solution in $H_2O$ sterilised by autoclaving) were added to give a final concentration of 20 g/L where described.

4. SHAKE FLASK CULTURE AND INDUCTION PROCEDURES 4.1 Host Strain W3110 with pAC tac Expression Vector Shake flask cultures were made in 250 ml Erlenmeyer baffled flasks containing 40 ml YEGLY medium seeded with 4 ml inoculum prepared as described in section 2. Cultures were incubated at 30° C. and 250 RPM in an orbital incubator. Induction of product expression was obtained at OD 600 nm=5 by adding a 40 μl aliquot of IPTG (200 mM, freshly prepared aqueous solution sterilised by filtration). Cultures induced at an OD 600 of 2.5 produced higher yields for certain fragments than those induced at 5. Addition of IPTG to cultures which had reached OD's of 6 or greater and had moved into the decline phase of growth did not induce product expression.

Culture supernatants were harvested by centrifugation 12 h post induction with IPTG.

4.2 Host Strain W3110 with the Dual Origin Expression Vector

Cultures were grown as described in Section 4.1. Induction of product expression was achieved by transferring flasks to an orbital incubator pre equilibrated at 40° C. when cultures had reached an OD of 5.

Culture supernatants were harvested by centrifugation 12 h post induction by temperature switching.

5. FERMENTOR CULTURE AND INDUCTION PROCEDURES 5.1 Host Strain W3110 with pAC tac Expression Vector 5.1.1 Complex medium fermentations Fermentations were made in YEGLY medium inoculated at a seeding density of 5% with the culture described in section 1. The culture pH was controlled at 7.0+/−0.05 by addition of 2M NaOH or 2M $H_2SO_4$. Temperature was maintained at 30° C. and dissolved oxygen tension (DOT) was controlled at a value >10% air saturation by automatic control of agitator speed. Aeration was set at 0.75 v/v/min. Oxygen utilisation rates and carbon dioxide evolution rates were determined from exhaust gas analysis performed by mass spectrometry. Product formation was induced by adding IPTG as a filter sterilised 1000× stock solution to a final concentration of 200 μM when the culture OD had reached 5.

Fermentations were run with and without chloramphenicol (25 μg/ml), no requirement for antibiotic selection in the fermentation medium has been demonstrated.

Culture supernatants were harvested 12 h post induction by centrifugation 4200 RPM max 240 mm (1–2 l fermentations) or by tangential flow filtration (15 l and 150 l fermentations). Clarification of broths was superior with tangential flow filtration (TFF).

5.1.2 Defined Medium Fermentations

Fermentations were made in medium SM6 or SM6A, glucose was used as the initial carbon and energy source for all fermentations and was added after medium sterilisation to a concentration of 20 g/l. Culture pH was brought to and maintained at 6.95 by the addition of 3.6M $NH_4OH$, or 2M $H_2SO_4$. DOT was maintained above 10% by control of agitator speed, culture temperature was maintained at 30° C. throughout the fermentation.

IPTG inductions: Cultures were induced with IPTG (final concentration 200 μM) at OD 600 nm=40. Cultures induced with IPTG were fed glucose as required, (either in response to OUR or as predicted by an approximate yield of 1 OD/g glucose/1).

Lactose inductions: Induction of product expression was also obtained by switching the carbon source to lactose from glucose. Glucose was fed to support the culture to an OD of approximately 30 (an accumulative addition of 30 g/l). Lactose feeding was started at an OD of approximately 25, as with glucose, lactose was then fed (normally as individual shots of 50% lactose to a concentration of 10 g/l culture) as required. The 50% lactose solution was held in a water bath at 55° C. after autoclaving to prevent crystallisation.

Cultures induced by IPTG were harvested 20 h post induction. Cultures induced by lactose feeding were harvested 24–30 h after the switch from glucose to lactose utilisation.

Where casamino acids were added to defined medium fermentations these additions were made 3 h post induction.

5.2 Host Strain W3110 with the Dual Origin Expression Vector 5.2.1 Complex medium fermentations These fermentations were made as described in section 5.1.1 except that induction of product formation was achieved by increasing the culture temperature when the OD had reached 20. A temperature switch to 37° C. from 30° C. and holding the culture at 37° C. was used.

5.2.2 Defined medium fermentations

These fermentations were made as described in section 5.1.2 except that glycerol was used throughout as the carbon and energy source (starting concentration 20 g/L). Medium SM6A could only be used with citrate reduced to 1 g/L total.

Fermentations run using glucose as the carbon source resulted in induction of product expression prior to temperature switching and in the absence of plasmid amplification.

Cultures were fed glycerol as required, again in response to the online OUR data or as predicted by an approximate yield of 1 OD/g glycerol/L.

Fermentations were harvested 12 h post temperature induction by centrifugation or TFF. Where inductions did not arrest growth (normally 4–6 h post temperature shift) it was not possible to maintain the DOT above 10% air saturation, these cultures were allowed to become oxygen depleted and harvested.

6. PERIPLASMIC EXTRACTION PROCEDURES

For certain antibody fragments significant quantities of material were retained within the cell periplasm. Product was released from the periplasm by incubating culture pellets or concentrated cell suspensions harvested by centrifugations or TFF respectively. Harvested cells were washed with phosphate buffered saline (PBS) and then incubated in Tris buffer 100 mM pH 7.2 containing 10 mM EDTA. Incubations were at 30° C. for 4 h. Repeated incubations of the cells produced further material.

EXAMPLE C

Fermentation Process for Expression of Antibody Fragments in *E. coli* W3110 Using Defined Medium and the Dual Origin Vector Storage of Strains As frozen cell suspensions (−70° C. and original OD 600 nm=2) in LB amp medium using 12.5% glycerol as a cryoprotectant.

Preparation of Inocula

Inocula were prepared from glycerol stock cultures. 200 ml aliquots of LB+amp (25 mg/l) were dispensed into sterile 1 l Erlenmeyer flasks and inoculated with 500 μl glycerol stock culture. These flasks were incubated at 30° C. and 250 RPM in an orbital incubator for approx 10 h or until an OD of 3 had been obtained. Fermentors were inoculated with LB cultures at 5% culture volume.

Fermentation Conditions

Culture medium SM6 chemically defined medium. No antibiotics were added to the SM6 medium other than carry over from the inoculum.

Carbon source: glycerol, initial concentration 20 g/l. When the culture OD reached 15, glycerol was fed as a 50% (w/w) solution in $H_2O$ at a rate of approx 5 g (glycerol)/l/h. This glycerol feed can alternatively be applied as a series of batch additions to maintain glycerol sufficiency. The glycerol requirement varies with varying growth response to induction.

Culture temperature was controlled at 30° C.+/−0.5° C. until the culture was induced at OD 10, 20 or 35 by switching the temperature to 37° C. where the temperature was maintained until harvest. The optimum temperature induction profile may vary significantly with different heterologous proteins.

Culture pH was controlled to 7.0+/−0.1 by the addition of 4M $NH_4$ OH or 2M $H_2$ $SO_4$.

Culture dissolved oxygen tension (DOT) was maintained at a value greater than 20% air saturation by regulations of the stirrer speed. Aeration was set at 0.75 v/v/m.

Cultures were harvested approx 8 h post induction.

Broths were clarified either by centrifugation (for volumes <2 l) or by tangential flow filtration (TFF) using a millipore prostack.

The invention is described above by way of example only, and various modifications will be apparent to those skilled in the art which fall within the scope of the appended claims.

We claim:

1. A method for the production of a heterologous protein in a bacterial host cell, comprising culturing a bacterial host cell transformed with an expression vector comprising a transcription unit encoding the heterologous protein, in order to express the heterologous protein, wherein said expression vector is controlled by a single origin of replication which maintains a vector copy number between 6 and 50, the transcription unit comprises a regulatable promoter and a transcriptional terminator, and the host cell is cultured in a defined medium in the absence of antibiotic selection.

2. A method according to claim 1, wherein said expression vector shows structural and segregational stability.

3. A method according to claim 1, wherein said transcription unit codes for an antibody molecule.

4. A method according to claim 3, wherein said transcription unit codes for (a) both an antibody heavy chain and an antibody light chain, or (b) both an antigen-binding fragment of an antibody heavy chain and an antigen-binding fragment of an antibody light chain.

5. A method according to claim 3, wherein said antibody is a humanised or CDR-grafted antibody molecule.

6. A method according to claim 4, wherein said transcription unit codes for a Fab or Fab' antibody fragment.

7. A method according to claim 1, wherein said expression vector further comprises a gene encoding a repressor which acts on said regulatable promoter to prevent expression of said transcription unit.

8. A method according to claim 1, wherein said transcription unit is fused to a DNA sequence encoding a secretion sequence.

9. A method according to claim 1, wherein said host cell is an *E. coli* cell.

10. A method according to claim 4, wherein said antibody is a humanised or CDR-grafted antibody molecule.

11. A method according to claim 5, wherein said transcription unit codes for a Fab or Fab' antibody fragment.

* * * * *